United States Patent [19]

Tsuji et al.

[11] Patent Number: 6,013,518
[45] Date of Patent: Jan. 11, 2000

[54] FUSED CELL LINE AND METHOD OF OBTAINING THE SAME

[75] Inventors: Kenkou Tsuji, Shizuoka-ken; Mari Yamamoto, Kakegawa; Kazuhiro Osada; Hiroharu Kawahara, both of Shimada, all of Japan

[73] Assignees: Director-General of National Research Institute of Vegetables, Ornamental Plants and Tea, Ministry of Agriculture, Forestry and Fisheries, Age-gun; Bio-oriented Technology Research Advancement Institution, Omiya, both of Japan

[21] Appl. No.: 09/001,995

[22] Filed: Dec. 31, 1997

[30] Foreign Application Priority Data

Oct. 22, 1997 [JP] Japan ..................................... 9-306360

[51] Int. Cl.⁷ ...................................................... C12N 5/08
[52] U.S. Cl. ........................................... 435/325; 435/440
[58] Field of Search ....................... 435/325, 440

*Primary Examiner*—Laurie Scheiner
*Attorney, Agent, or Firm*—Oblon, Spivak, McClelland, Maier & Neustadt, P.C.

[57] ABSTRACT

Provided are a human immunocompetent fused cell line, characterized in that any one of a mutant cell selected from the group consisting of ICLU-B, ICLU-T and ICLU-E is used as a parent cell line, wherein said mutant cell is obtained by selecting an 8-azaguanine- or 6-thioguanine-resistant clone from a human Burkitt lymphoma cell line Raji, a human T-cell lymphocytic leukemia cell line PEER and a human eosinophilic leukemia cell line EoL-1, and then treating said clone in order to capable of serum-free culture, and a method of obtaining said human immunocompetent fused cell line.

The human immunocoipetent fused cell line obtained by the present invention is used to investigate food functions, novel drugs and production thereof with the view to the elucidation of mechanisms of phenomena of an immune system such as allergies, cancers and the like using human cell lines, and the prevention, diagnosis and therapy of these diseases.

3 Claims, No Drawings

FUSED CELL LINE AND METHOD OF OBTAINING THE SAME

FIELD OF THE INVENTION

The present invention relates to a fused cell line and a method of obtaining the same. More specifically, the present invention relates to a human immunocompetent fused cell line which is used to investigate food functions, novel drugs and production thereof with a view to the elucidation of mechanisms of phenomena of an immune system such as allergies, cancers and the like using human cell lines, and the prevention, diagnosis and therapy of these diseases.

BACKGROUND OF THE INVENTION

The in vitro incubation of cells separated from the human body is difficult in many cases. For example, it is difficult to infinitely grow cells, such as lymphocytes, separated from the human body in vitro. Usually, even when these cells are incubated in a culture medium, they are died within from 2 weeks to several months. Some cancer cells or epithelial cells can be subcultured in vitro in a medium having some formulation. However, it is hard to obtain the same in an amount sufficient for investigation.

Further, in order to grow internal cells in vitro, it is necessary to exert some stimulus on cells. Thus, a variety of physiologically active substances have to be added to a culture medium. However, the selection of the appropriate substance is problematic, and it takes much labor.

In recent years, In order to solve these problems, a method has been proposed in which a carcinogenic substance or the like is added to desired cells or these cells are irradiated with ultraviolet rays or radiation for mutageniza ion (transformation).

Such a treatment can provide cell lines (mutant strains) capable of infinite growth.

Further, a method has been also proposed in which cancer genes are injected into desired cells by a gene transfer method to cause transformation, obtaining cells which are infinitely grown.

Still further, besides the method using the transformation, a method has been also known in which cells that produce antibodies or immunomodulation factors (lymphokines) in vivo are fused with cells to be infinitely grown to establish fused cells (hybridomas) producing antibodies or immunomodulation factors in vitro.

These conventional methods have, however, involved the following problems.

First, in the method using chemicals or the method using the irradiation with ultraviolet rays or the like, it takes much time, from several months to several years, to establish cell lines which are stable in the mutagenicity obtained and other cell functions. Further, it takes considerable time to put cell lines established to practical use. Further, the number of mutant strains (mutagenization efficiency) obtained relative to the number of cells treated is small. Thus, it is difficult to easily establish cell lines from objective cells.

Further, the method of obtaining cell lines through cell fusion is useful in a stable system of producing cell-derived substances such as monoclonal antibodies, lymphokine or the like. However, in the fused cell lines obtained by this method, the cell response is said to be decreased or lost against in various immuno-reactions which occur in vivo.

Accordingly, it has been quite difficult to use the in vivo cell interaction in a reproducible cell system in vitro even by these methods.

SUMMARY OF THE INVENTION

The present inventors have conducted investigations on a method of obtaining cell lines, and have focused on the fact that formation of cell lines through cell fusion provides a relatively high transformation efficiency as compared to other methods. However, it is known that the properties of cell lines obtained through the cell fusion greatly depend on not only human immunocompetent cells subjected to the fusion but also human parent cell lines as the other partner.

Therefore, the present inventors have studied parent cell lines in order to establish cell lines from various human immunocompetent cells at good efficiency while maintaining cell functions, and they have established three types of cell lines; cell line ICLU-B derived from a human Burkitt lymphoma, cell line ICLU-T derived from a human T-cell lymphocytic leukemia and cell line ICLU-E derived from a human eosinophilic leukemia all of which are mutant strains.

It has been clarified that fused cells obtained by fusing these human parent cell lines with a variety of human in vivo immunocompetent cells still retain cell functions which these cells are considered to exhibit in vivo.

Further, it has been clarified that among these parent cell lines for cell fusion, ICLU-T can not conduct efficient cell fusion in a well-known cell fusion accelerator (polyethylene glycol, hereinafter referred to as "PEG") and in a fusion cell selective medium (HAT medium) in which only fused cells are grown.

Accordingly, the present inventors have investigated a method of obtaining fused cells using ICLU-T as a parent cell line. Consequently, they have developed a fusion accelerator containing a mixture of PEG and lecithin, a phospholipid, and a selective medium comprising hypoxanthine and amethopterin. As a result, it has been found that the cell fusion can be conducted at good efficiency using the same.

Incidentally, the parent cell lines for human cell fusion, ICLU-B, ICLU-T and ICLU-E which are used in the present invention can be fused with not only the immunocompetent cells but also the cells derived from other tissues.

Thus, the first invention is to provide a human immunocompetent fused cell line, characterized in that any one of a mutant cell selected from the group consisting of ICLU-B, ICLU-T and ICLU-E is used as a parent cell line, wherein said mutant cell is obtained by selecting an 8-azaguanine- or 6-thioguanine-resistant clone from a human Burkitt lymphoma cell line Raji, a human T-cell lymphocytic leukemia cell line PEER and a human eosinophilic leukemia cell line EoL-1, and then treating said clone in order to capable of serum-free culture.

The second invention is to provide a method of obtaining a human immunocompetent fused cell line, which comprises forming a fused cell by using a parent cell line for human cell fusion, ICLU-T and a human immunocompetent cell in the presence of polyethylene glycol and lecithin.

DETAILED DESCRIPTION OF THE INVENTION

The properties of fused cell lines, as stated above, greatly depend on not only human immunocompetent cells subjected to the fusion but also parent cell lines. Accordingly, the present inventors have established parent cell lines for human cell fusion which can be used to form cell lines from a variety of human immunocompetent cells at good efficiency while maintaining the cell functions. That is, the parent cell lines have been obtained from human immunocompetent cells as follows.

A human Burkitt lymphoma cell line (Raji), a human T-cell lymphocytic leukemia cell line (PEER) and a human eosinophilic leukemia cell line (EoL-1) which are human cell lines already established were incubated in a 10% FBS-ERDF medium (supplied by Kyokuto Seiyaku Kogyo K. K.) containing 6-thioguanine (final concentration 30 $\mu$g /ml) or 8-azaguanine (final concentration 20 $\mu$g/ml).

After approximately 3 weeks of the incubation, clones grown were collected, and the cloning was conducted by a limiting dilution method in which a cell suspension was diluted and included using a 10% FBS-ERDF medium such that one cell was put in one well of a 96-well culture plate. The clones which were grown earliest in the cloning were recloned by the same method.

After the parent cell line was established, the clones obtained through the cloning were incubated in an ERDF medium (supplied by Kyokuto Seiyaku Kogyo K.K.) containing insulin (final concentration 10 $\mu$g/ml), transferrin (final concentration 20 $\mu$g/ml), ethanolamine (final concentration 20 $\mu$M) and sodium selenite (final concentration 25 nM) such that the fused cells obtained through the cell fusion could be subjected to serum-free culture. At this time, the incubation was conducted for approximately 2 weeks through dilution such that one cell was charged in one well of a 96-well incubation plate.

Among the clones grown, the clones which were grown at the highest speed and which were died in the incubation in a 15% FBS-ERDF medium containing aminopterin were established as candidates of parent cell lines.

The cell fusion was actually conducted using the resulting clones which became candidates of the parent cell lines, and the clones from which fused cells were obtained at the highest efficiency were selected as parent cell lines.

With respect to the thus-established three types of parent cell lines, namely, the Raji-derived parent cell line was designated a human Burkitt lymphoma derived cell line (ICLU-B), the PEER-derived parent cell line a human T-cell lymphocytic leukemia derived cell line (ICLU-T) and the EoL-1-derived parent cell line a human eosinophilic leukemia derived cell line (ICLU-E) respectively. ICLU-B, ICLU-T and ICLU-E were deposited under the terms of the Budapest Treaty at National Institute of Bioscience and Human-Technology (NIBH), Agency of Industrial Science and Technology, Ministry of International Trade and Industry, 1-3, Higashi 1-chome, Tsukaba-shi, Ibaraki-ken 305, Japan, under the accession numbers FERM BP-6253, FERM BP-6255 and FERM BP-6254, respectively.

The fused cell line in the first invention can be obtained by fusing one of these parent cell lines with the human immunocompetent cell such as a human peripheral blood lymphocyte.

The fusion of the parent cell line and the human immunocompetent cell can be conducted in the following manner, for example.

First, any one of the above-mentioned parent cell lines is mixed with the human immunocompetent cell. As the human immunocompetent cell to be fused with the parent cell line, any cell having an immunological function in the human body can be used. For example, a human lymphocyte is available.

The ratio of the huian immunocompetent cell to the parent cell line is preferably between 1.5 and 2 times when using ICLU-B as a parent cell line, between 0.8 and 1.2 times when using ICLU-T, and between 1 and 1.5 times when using ICLU-E.

The fusion can also be conducted using, instead of the human immunocompetent cell, cells derived from other human tissues, for example, a human cancer cell. When using the cancer cell, the type of the tissue from which the cancer cell is deriveed is not particularly limited. For example, a gastric cancer cell or a breast cancer cell can be used. In this case, the ratio of this cell to the parent cell line may be the same as the above-mentioned ratio.

The mixture of the parent cell line and the human immunocompetent cell is centrifuged to separate it into the supernatant and the cell pellets. Of these, the supernatant is removed. To the residual cell pellets is added PEG (fusion accelerator) which is diluted (usually to between 40 and 50%) with a basic synthetic medium.

Examples of the basic synthetic medium include an ERDF medium, an RPMI 1640 medium, and a Dalbecco modified Eagle's medium (DMEM). It is also possible to use, along with this medium, fetal bovine serum (FBS) as a growth factor, or a growth factor for serum-free culture, such as insulin, transferrin, ethanolamine or sodium selenite.

Further, PEG having an average molecular weight of from 4,000 to 6,000 can be used as a fusion accelerator. In view of a fusion efficiency, PEG having an average molecular weight of 4,000 is preferable. In the case of using ICLU-T, PEG having an average molecular weight of 4,000 is especially preferable.

When ICLU-T is used as a parent cell line, a mixture of PEG and lecithin has to be used as a fusion accelerator.

When the cell fusicn is conducted using ICLU-T without mixing PEG with lecithin, the disruption of a cell membrane of ICLU-T notably occurs, the number of liaving cells left is decreased, and the desired fused cell cannot be obtained at good efficiency.

Lecithin is a type of a phospholipid which is a main component of the cell membrane. When the cell fusion using ICLU-T is conducted with a mixture of PEG and this lecithin, the phospholipid which is a main component of the cell membrane is protected, making it possible to control the disruption of the cell membrane caused by PEG as much as possible.

The cell pellets containing the fusion accelerator diluted with the medium are centrifuged, and the fused cells are then selected from the cell pellets.

The selection of the fused cells when using ICLU-B or ICLU-E as a parent cell line can be conducted in a well-known selective medium (for example, a 15% FBS-ERDP medium) containing hypoxanthine, aminopterin (amethopterin is also available) and thymidine.

After from 24 to 30 hours of the fusion, a selective medium containing hypoxanthine), aminopterin and thymidine is added to the fused cells. In this case only, the concentrations of these substances in the selective medium are doubled. Thereafter, the medium having the same formulation as the initial selective medium is replaced by half every several days.

This incubation is conducted for approximately 2 weeks to be able to obtain the fused cells.

Meanwhile, when using ICLU-T as a parent cell line, the selection of fused cells is conducted basically in the above-mentioned manner. However, this selection is different from the above-mentioned selection using ICLU-B or ICLU-E in that the former uses a selective medium containing hypoxanthine and aminopterin but not thymidine.

When thymidine is present in the selective medium in using ICLU-T as a parent cell line, the growth inhibition occurs. For this reason, the addition of thymidine has to be avoided.

After from 24 to 30 hours of the fusion, a selective medium (for example, a 15% FBS-ERDF medium) containing hypoxanthine and aminopterin is added to the suspension. This medium is, like the above-mentioned medium, replaced by half every several days.

The fused cells can be obtained through this incubation for approximately 2 weeks.

The fused cells obtained from the parent cells through the fusion can retain in vitro the specific immuno-reaction (cell function) that the corresponding immunccompetent cells express in vivo.

The human immunocompetent fused cell line of the present invention which is formed using any of ICLU-B, ICLU-T and ICLU-E as a parent cell line expresses in vitro an immunological function that the corresponding immuno-competent cells exhibit in vivo and the other properties as such.

Further, when the fused cells are formed from ICLU-T and human immunocompetent cells in the presence of polyethylene glycol and lecithin according to the method of the second invention, a cell line of fused cells which retain the immunological function in vivo as such can be established at good efficiency.

The fused cell line of the present invention can preferably be used to study the in vivo intercellular reaction in vitro.

EXAMPLES

The present invention is illustrated specifically by referring to the following typical Examples. However, the present invention is not limited thereto.

Example 1

Formation of a human lymphocyte cell line using ICLU-B:

A parent cell line ICLU-B having a cell concentration of $1 \times 10^7$ was mixed with $2 \times 10^7$ human peripheral blood lymphocytes. The mixture was centrifuged, and the supernatant was separated from cell pellets. Subsequently, this supernatant was removed.

To the remaining cell pellets was added 1 ml of 50% PEG (average molecular weight: 4,000) diluted with an ERDF medium (supplied by Kyokuto Seiyaku Kogyo K.K.). Further, 9 ml of the ERDF medium were added thereto so that the total volume was adjusted to 10 ml.

The mixture was recentrifuged, and the resulting cell pellets were suspended in 50 ml of a 15% FBS-HRDF medium which had been prepared such that the ERDF medium was 85% and fetal bovine serum was 15%. The suspension was added to a 96-well incubation plate such that 100 µl of the suspension were charged in each well of the plate.

On the following day of the fusion, a 15% FBS-ERDF medium containing 400 µM hyfpoxanthine, 0.8 µM amethopterin and 32 µM thymidine was added to a 96-well incubation plate such that 100 µg of the medium were charged in each well of the plate. Then, this medium was replaced with a 15% FBS-ERDF medium containing 200 µM hypoxanthine, 0.4 µM amethopterin and 16 µM thymidine by half every 2 or 3 days.

After 2 weeks of the incubation, the number of wells in which the fused cells of ICLU-B and human peripheral blood lymphocytes appeared and the fusion efficiency were measured. The results are shown in Table 1.

Further, the cell fusion was conducted in the above-mentioned manner except using ICLU-B having a cell concentration of $3 \times 10^6$ and $6 \times 10^6$ human peripheral blood lymphocytes. The results are also shown in Table 1.

The properties of the resulting fused cells were measured as follows.

First, an anti-B cell antibody, an anti-T cell antibody and an anti-monocyte antibody which were all fluorescent were used, and it was examined which antibody the fused cells were reacted with. From the results, it could be known whether the fused cells were B-cellular, T-cellular or monocytic.

When the fused cells were B-cellular in the examination using the antibodies, it was further identified whether the fused cells had an antibody (Ig)-productivity.

When the fused cells were T-cellular, it was further identified into what sub-set the fused cells were classified. When the fused cells were monocytic, it was further identified whether they had a phagocytic activity.

The types of the fused cells obtained by the above-mentioned two fusion procedures and the average values of the ratios and the like are shown in Table 2.

Example 2

Formation of a human lymphocyte line using ICLU-T:

ICLU-T having a cell concentration of $4 \times 10^6$ was mixed with $4 \times 10^6$ human peripheral blood lymphocytes. The mixture was centrifuged, and the supernatant was separated from cell pellets. Subsequently, this supernatant was removed.

To the cell pellets was added 1 ml of 40% PEG (average molecular weight: 4,000) mixed with 1% lecithin. Further, 9 ml of the ERDF medium were added thereto so that the total volume was adjusted to 10 ml.

The mixture was recentrifuged, and the resulting cell pellets were suspended in 25 ml of a 15% FBS-ERDF medium which had been prepared such that the ERDF medium was 85% and fetal bovine serum was 15%. The suspension was added to a 96-well incubation plate such that 100 µl of the suspension were charged in each well of the plate.

After 4 days of this fusion, a 15% FBS-ERDF medium containing 133 µM hypoxanthine and 0.26 µM amethopterin was added to a 96-well incubation plate such that 100 µl of the medium were charged in each well of the plate. Then, this medium was replaced with a 15% FBS-ERDF medium containing 67 µM hypoxanthine and 0.13 µM amethopterin by half every 4 or 5 days.

After 2 weeks of the incubation, the number of wells in which the fused cells of ICLU-T and human peripheral blood lymphocytes appeared and the fusion efficiency were measured. The results are shown in Table 1.

Further, the cell fusion was conducted in the above-mentioned manner except using ICLU-T having a cell concentration of $5 \times 10^6$ and $5 \times 10^6$ human peripheral blood lymphocytes. The results are also shown in Table 1.

The properties of the resulting fused cells were measured in the same manner as in Example 1. The results are shown in Table 2.

Example 3

Formation of a human lymphocyte cell line using ICLU-E:

ICLU-E having a cell concentration of 1×10⁷ was mixed with 1×10⁷ human peripheral blood lymphocytes. The mixture was centrifuged, and the supernatant was separated from cell pellets. Subsequently, this supernatant was removed.

To the remaining cell pellets was added 1 ml of 40% PEG (average molecular weight: 4,000) diluted with an ERDF medium. Further, 9 ml of the ERDF medium (supplied by Kyokuto Seiyaku Kogyo K.K.) were added thereto so that the total volume was adjusted to 10 ml.

The mixture was recentrifuged, and the resulting cell pellets were suspended in 50 ml of a 15% FBS-ERDF medium which had been prepared such that the ERDF medium was 85% and fetal bovine serum was 15%. The suspension was added to a 96-well incubation plate such that 100 μl of the suspension were charged in each well of the plate.

On the following day of this fusion, a 15% FBS-ERDF medium containing 400 μM hypoxanthine, 0.8 μM amethopterin and 32 μM thymidine was added to a 96-well incubation plate such that 100 μl of the medium were charged in each well of the plate. Then, this medium was replaced with a 15% FBS-ERDF medium containing 200 μM hypoxanthine, 0.4 μM amethopterin and 16 μM thymidine by half every 2 or 3 days.

After 2 weeks of the incubation, the number of wells in which the fused cells of ICLU-E and human peripheral blood lymphocytes appeared and the fusion efficiency were measured. The results are shown in Table 1.

Further, the cell fusion was conducted in the above-mentioned manner except using ICLU-E having a cell concentration of 7×10⁸ and 7×10⁶ human peripheral blood lymphocytes. The results are shown in Table 1.

The properties of the resulting fused cells were measured in the same manner as in Example 1. The results are shown in Table 2.

TABLE 1

| | Type of a parent cell line | Number of cells of a parent cell line | Number of wells in which fused cells appeared | Fusion efficiency (per 10⁵ cells of a parent cell line) |
|---|---|---|---|---|
| Example 1 | ICLU-B | 1 × 10⁷ | 130 | 1.3 |
| | | 3 × 10⁶ | 30 | 1.0 |
| Example 2 | ICLU-T | 4 × 10⁶ | 8 | 0.2 |
| | | 5 × 10⁶ | 9 | 0.18 |
| Example 3 | ICLU-E | 1 × 10⁷ | 48 | 0.48 |
| | | 7 × 10⁶ | 15 | 0.21 |

TABLE 2

| | Parent cell line | Types of the cells of the fused cell line obtained and the ratio thereof | | Remarks |
|---|---|---|---|---|
| Example 1 | ICLU-B | B cells: | 72.3% | IgG, IgM and IgE are produced. |
| | | T cells: | 18.2% | |
| | | Monocytes: | 9.5% | |
| Example 2 | ICLU-T | B cells: | 11.1% | Helper-type |
| | | T cells: | 77.8% | |
| | | Monocytes: | 11.1% | |
| Example 3 | ICLU-E | B cells: | 20% | Ig is not produced. |
| | | T cells: | 57.1% | A phagocytic activity is exhibited. |
| | | Monocytes: | 22.9% | |

From Table 1, it was identified that any of the parent cell lines could provide the fused cells with the human peripheral blood lymphocytes at high efficiency through the incubation for 2 weeks.

Further, Table 2 reveals the following.

First, it is clarified that any of the three parent cell lines can form cell lines of various immunocompetent cells in vivo.

When ICLU-B is used as a parent cell line of fused cells, any of the three immunocompetent cells can be obtained. Mainly, the B cells are provided. The fused cell line of the B cells obtained from ICLU-B has an Ig-productivity. Thus, it is identified that this cell line retains the properties of the B lymphocytes which are antibody-productive cells among peripheral blood lymphocytes subjected to the fusion.

Further, when ICLU-T is used as a parent cell line in the cell fusion, the fused cells of the T cell type are mainly obtained. These fused cells of the T cell type are of the helper type. Accordingly, it is identified that these fused cells retain the properties of the T lymphocytes among the peripheral blood lymphocytes subjected to the cell fusion.

However, when ICLU-E is used as a parent cell line of fused cells, the resulting fused cells chiefly exhibit the properties of the T cell type. However, as compared to the case of using ICLU-B or ICLU-T as the parent cell line, a large number of monocytic fused cells are obtained.

Since this fused monocytic line has a phagocytic activity, it is identified that this cell line retains the properties of the monocytes.

Example 4

Examination of a fusion accelerator when cell fusion is conducted using a parent cell line ICLU-T:

ICLU-T cells and human peripheral blood lymphocytes were mixed such that a ratio of numbers of these cells was 1:1 (specific value is shown in Table 3). This mixture was centrifuged, and the supernatant was separated from cell pellets. This supernatant was then removed.

To the cell pellets was then added 1 ml of a mixture of 1% lecithin and 40% PEG (average molecular weight: 4,000) prepared using an ERDF medium (supplied by Kyoktuto Seiyaku Kogyo K.K.) as a basic medium and 1% lecithin. Further, 9 ml of an ERDF medium were added thereto so that the total volume was adjusted to 10 ml.

The mixture was recentrifuged, and the resulting cell pellets were suspended in 50 ml of a 15% FBS-ERDF medium which had been prepared such that the ERDF medium was 85% and FBS was 15%. The suspension was added to a 96-well incubation plate such that 100 μl of the suspension were charged in each well of the plate.

After 4 days of the fusion, a 15% FBS-ERDF medium containing 133 μM hypoxanthine and 0.26 μM amethopterin was added to a 96-well incubation plate such that 100 μl of the medium were charged in each well of the plate. Then, this medium was replaced with a 15% FBS-ERDF medium containing 67 μM hypoxanthine and 0.13 μM amethopterin by half every 4 or 5 days.

After 2 weeks of the incubation, the number of wells in which the fused cells of ICLU-T and human peripheral blood lymphocytes appeared and the fusion efficiency were measured. The results are shown in Table 3.

On the other hand, as a control, the cell fusion was conducted in the above-mentioned manner except using 40% PEG (average molecular weight: 4,000) diluted with a lecithin-free ERDF medium. The results are also shown in Table 3.

TABLE 3

| Formulation of a fused accelerator | Number of cells subjected to fusion | Number of wells in which fused cells appeared | Fusion efficiency* |
|---|---|---|---|
| PEG + lecithin | $4 \times 10^6$ | 8 | 0.20 |
|  | $5 \times 10^6$ | 9 | 0.18 |
| PEG alone | $1 \times 10^7$ | 2 | 0.02 |
|  | $5 \times 10^6$ | 0 | 0 |
|  | $7 \times 10^6$ | 1 | 0.01 |

*per $10^5$ parent cells

Table 3 reveals that when PEG alone is used as a fusion accelerator, no fused cell is obtained or the fusion efficiency is quite low even when fusion cells are provided. Meanwhile, it is clear that when both PEG and lecithin are used, the fused cells can be obtained at good efficiency.

From the above-mentioned results, it is clarified that when the cell fusion is conducted using ICLU-T as a parent cell line, both PEG and lecithin have to be added as a fusion accelerator.

What is claimed is:

1. A human immunocompetent fused cell line wherein
   (a) a mutant cell is obtained by selecting an 8-azaguanine- or 6-thioguanine- resistant clone from
      (i) a human Burkitt lymphoma cell line Raji, wherein said mutant cell is ICLU-B,
      (ii) a human T-cell lymphocytic leukemia cell line PEER, wherein said mutant cell is ICLU-T, or
      (iii) a human eosinophilic leukemia cell line EoL-1, wherein said mutant cell is ICLU-E; and
   (b) said mutant cell is fused to a human immunocompetent cell, wherein said human immunocompetent fused cell line can be incubated in serum-free culture.

2. The human immunoconipetent fused cell line of claim 1, wherein prior to fusion with said human immunocompetent cell, the mutant cell is incubated in an ERDF medium containing insulin, transferrin, ethanolamine and sodium selenite.

3. A method of obtaining a human immunocompetent fused cell line, which comprises fusing a parent cell line ICLU-T and a human immunocompetent cell in the presence of polyethylene glycol and lecithin.

* * * * *